(12) United States Patent
Le

(10) Patent No.: US 7,018,591 B2
(45) Date of Patent: Mar. 28, 2006

(54) HIGH HEAT TRANSFER TUBULAR REACTOR

(75) Inventor: Vinh N. Le, Riyadh (SA)

(73) Assignee: Saudi Basic Industries Corporation, Riyadh (SA)

( * ) Notice: Subject to any disclaimer, the term of this patent is extended or adjusted under 35 U.S.C. 154(b) by 938 days.

(21) Appl. No.: 10/046,109

(22) Filed: Jan. 12, 2002

(65) Prior Publication Data

US 2003/0133858 A1  Jul. 17, 2003

(51) Int. Cl.
*F28D 7/00* (2006.01)
*B01J 10/00* (2006.01)

(52) U.S. Cl. ............... 422/201; 188/190; 188/191; 188/192; 188/196; 188/197; 188/200; 188/201

(58) Field of Classification Search ............ 422/188, 422/191, 192, 196, 197, 200, 201
See application file for complete search history.

(56) References Cited

U.S. PATENT DOCUMENTS

| | | | |
|---|---|---|---|
| 2,778,610 A | 1/1957 | Bruegger | |
| 2,978,797 A | 4/1961 | Ekelund | |
| 3,154,141 A | 10/1964 | Huet | |
| 3,289,644 A | 12/1966 | Kodaira | |
| 3,930,941 A | 1/1976 | Meerwald | |
| 4,923,306 A | 5/1990 | Faurke | |
| 5,027,891 A | 7/1991 | Fulford | |
| 5,071,627 A | 12/1991 | Child | |
| 5,195,575 A | 3/1993 | Wylie | |
| 6,808,689 B1 * | 10/2004 | Matsumoto et al. | 422/196 |

OTHER PUBLICATIONS

Patent Abstracts of Japan, vol. 009, No. 317 (C–319), Dec. 12, 1985, JP 60153936, Babcock Hitachi KK.
Patent Abstracts of Japan, vol. 013, No. 273 (C–609), Jun. 22, 1989, JP01067246, Mitsubishi Electric Corp.

* cited by examiner

*Primary Examiner*—Glenn Caldarola
*Assistant Examiner*—Alexis Wachtel
(74) *Attorney, Agent, or Firm*—Kramer Levin Naftalis & Frankel LLP

(57) ABSTRACT

A vapor-phase tubular reactor in a shell heat exchanger for removal of the heat of reaction at essentially isothermal conditions has porous wicking surface applied to the external surface of reactor tubes. The porous wicking surface on the reactor tubes draws liquid heat transfer fluid from a reservoir at the bottom of the wicked tube section and provides enhanced evaporative cooling. The invention is particularly useful for highly exothermic reactions or when reaction selectivity is negatively affected by high temperature excursions.

14 Claims, 3 Drawing Sheets

HIGH HEAT TRANSFER TUBULAR REACTOR

BACKGROUND OF THE INVENTION

1. Field of the Invention

This invention relates to a tubular reactor integrated with an heat exchange apparatus particularly well suited for removing large amounts of heat from the reactor at essentially isothermal conditions.

2. Background of the Invention

A variety of commercially important chemical reactions, and in particular catalytic vapor-phase partial oxidation reactions, are performed in tubular reactors in which maintaining the temperature of the reactants within a narrow temperature range is critical for achieving desired product yield, selectivity and properties. Many of these reactions are fast and highly exothermic. Such reactions are conventionally conducted at elevated temperature in heterogeneous catalytic tubular reactors. Most often such reactors are built as shell and tube heat exchangers in which the tubes are filled with an appropriate catalyst supported on a porous medium. Gas reactants are fed into the reactor tubes where they flow past the catalyst and react to form the desired product. The heat of reaction is quickly transferred from the site of the reaction to the outside walls of the tubes. A circulating or boiling coolant on the shell side removes the heat of reaction. Conventionally, the oxygen content of the reactants is kept low to stay outside of the explosive limit of the hydrocarbon—oxygen mixture and to minimize the formation of the complete oxidation by-product, carbon dioxide.

Two methods of cooling are customarily used with tubular reactors, forced circulation or the boiling of a suitable heat transfer fluid. Poor heat transfer between the reactor tubes and the heat transfer fluid often results in an undesirable temperature profile along the reactor tube length. Typically, the temperature profile of an exothermic catalytic reaction is low at the feed end, rises to a maximum at a central tube section and then drops off as the reaction is starved of reactants. Thus, vapor-phase fixed-bed tubular catalytic reactors exhibit a pronounced and undesirable temperature "hump" or the "hot spot".

Reactor temperatures which exceeds the optimum temperatures for a given reaction result in lower selectivity as undesirable products are formed. Undesirable side reactions also lead to localized high temperature hot spots which can carbonize organic heat transfer fluids. One reaction in which this can occur is the highly exothermic partial oxidation of ethylene to ethylene oxide where the heat transfer fluid is typically DOWTHERM or tetrahydronaphtalene or similar HTF.

The temperature profile of a catalytic tubular reactor often changes with time as the catalyst deactivates. In general, a catalytic tubular reactor's hot spot tends to move from its inlet end to its outlet end. Several methods have been proposed to control hot spots in catalytic tubular reactors, but all are deemed to be undesirable as either impractical or because they have the undesirable side effect of decreasing selectivity. Examples of such prior art methods are:

Gelbein (U.S. Pat. No. 4,261,899) proposed the use a dilute phase transported-bed (riser reactor) with a variable diameter and a fluidized-bed heat exchanger.

M. Yoshida and S. Matsumoto, (Journal of Chemical Engineering of Japan, Vol. 31, No. 3, pp. 381–390, 1998) suggested a single tube reactor with multiple electrical heaters.

A. I. Anastasov and V. A.Nikolov, (Industrial. Eng. Chem. Research. No. 37, pp. 3424–3433, 1998) disclose the use of dual reactors in series to optimize the overall performance.

Patent DE 3,935,030, JA 60-7929 and EP 339,748 describe reactors where cooling coils are embedded within the catalyst bed. This solution is impractical because of the very small tube size (between 20–40 mm) required for heat transfer.

In U.S. Pat. No. 5,262,551 methane is employed as a ballast gas instead of nitrogen. Methane has better heat capacity and conductivity leading to better gas heat transfer. Catalyst temperature is said to be reduced by 7° C.

U.S. Pat. No. 4,642,360 teaches a method whereby inert catalyst support is used to preheat the incoming gas.

No prior art is known to have taught a way to deal with localized hot spots which develop when gas flow is reduced due to maldistribution of gas or excessive pressure drop in a particular tube, or when the catalyst is locally over active, or when local heat transfer is impaired. The problem of localized hot spots can be particularly troublesome if the heat transfer fluid degrades into carbon blocks. Accordingly, it would be desirable if there were available a reactor for vapor-phase fixed bed catalytic reactions with improved heat removal capability, suitable to maintain an essentially isothermal temperature profile throughout the length of the reactor regardless of the heat load in individual tubes. It would also be desirable if such a reactor were to be easy to construct, operate and maintain. It would further be desirable if the heat of reaction could be recovered to generate steam. Further, to facilitate the charging of new catalyst and the punch out of used catalyst, the reactor should employ vertical tubes with lengths not exceeding about 35 ft. to 50 ft.

SUMMARY OF THE INVENTION

The chemical reactor of the present invention comprises a tubular reactor integrated with a heat transfer device commonly referred to as a heat pipe. As described in U.S. Pat. No. 2,350,348 to Gaugler, heat pipes utilize evaporation of a heat transfer fluid from a porous medium affixed to a heat transfer surface to absorb heat. In the present invention, a heat pipe system is applied to at least part of the external surface of a tubular reactor opposite the reaction mixture in the reactor's tubes to remove the heat of reaction from the reaction mixture by evaporative cooling from the heat transfer surface of the heat pipe system. The porous medium on the heat transfer surface is commonly referred to as a "wick". The evaporation of the heat transfer fluid from the porous medium or wick enjoys extremely good heat transfer coefficients and enables extremely high heat flux at essentially isothermal conditions. If desired, the evaporated heat transfer fluid is condensed and returned to the heat transfer zone of the reactor. Since heat transfer coefficients associated with condensation are also high, both the heat absorption and heat release segments of the heat pipe equipped reactor enjoy very high heat flux rates.

The benefits of utilizing a heat pipe heat transfer device on a tubular reactor as described are derived from its converting what would otherwise be convection heat transfer or conventional bare tube evaporative cooling to evaporative cooling of a thin film from a porous surface from which the evaporated heat transfer fluid can quickly and easily escape. Convection heat transfer is limited by many factors, including the velocity of the heat transfer fluid, the temperature differential between the reaction mixture and the cooling fluid, the viscosity of the heat transfer fluids, the surface area available for heat transfer, the materials of construction of the heat transfer device and the condition of the heat transfer surfaces, i.e., whether they are fouled. Conventional submerged tube evaporative cooling enjoys much higher heat transfer coefficients than convection cooling, but is limited by the liquid phase surrounding the submerged tubes. The heat pipe substitutes thin film evaporation for immersed tube boiling with a corresponding improvement of the shell side heat transfer coefficient of up to 10 times. Further, the heat release segment of the heat pipe equipped tubular reactor relies upon the condensation of the heat transfer fluid which can take place in a condenser which is remote from the reactor, so that the surface area available for cooling need not be limited to the area of the tubular reactor surface. Accordingly, condenser(s) with sufficient surface area to handle the required heat flux can be located away from the tubular reactor of the invention while still being in close proximity to it.

Because the evaporation of a pure heat transfer fluid occurs at a single temperature and the heat transfer coefficients for the heat pipe heat transfer system of the present invention are very good, a tubular reactor equipped with a heat pipe heat exchange device according to the present invention can be operated at essentially isothermal conditions. Because the heat transfer coefficients for thin film heat pipe evaporation are significantly higher than those for immersed tube evaporation, the reactor of the present invention enjoys substantially greater heat flux than would be possible with conventional cooling.

As described by Faghri ("Heat Pipe Science and Technology", Taylor and Francis, 1995) and by Peterson ("An Introduction to Heat Pipes", John Wesley & Sons, 1994), the choice of the material of construction, the choice of the heat transfer fluid and the design of the wick structure for the heat pipe apparatus of the invention are within the capability of those skilled in the art. The materials of construction in contact with the heat transfer fluid are commonly selected from copper and copper alloys, aluminum and its alloys and stainless steels.

Although the term heat "pipe" is used in the description of this invention, innumerable configurations are possible, some of which are far from the cylindrical shape of a conventional pipe. For example, possible shapes could be, but are not limited to, flat, rectangular, annular, polygonal or tubular.

The heat pipe heat transfer system of the present invention is comprised of two or three sections: (1) an evaporator section where heat is absorbed by vaporizing a liquid heat transfer fluid, (2) an adiabatic section where the vaporized heat transfer fluid flows without changing state, and optionally, (3) a condenser section where the vaporized heat transfer fluid is condensed using an external source of cooling. The heat transfer fluid condensate can be returned to the evaporator section of the tubular reactor by gravity or by pumping. In the evaporator section of the heat pipe heat transfer system of the invention, heat transfer fluid is supplied to a reservoir at the bottom of the wicked heat pipe surface where the wicking action of the porous surface or wick wets the heat pipe with a thin film of heat transfer fluid. Because wicking is a surface tension phenomenon which can be limited in long heat pipes by liquid head, it is sometimes preferred for a tubular reactor of the invention to have a heat pipe heat transfer section which is divided into multiple heat pipe heat transfer zones, each having a wick height which can be wetted by capillary action of the heat transfer fluid in the wick.

In one embodiment of the invention a source of liquid heat transfer fluid, which advantageously can be clean boiler feed water, feeds the heat pipe evaporator section of the reactor and the evaporator section communicates with a vapor header, such as a steam header. In this way, a tubular reactor according to the invention can be used to generate useful steam from reactor waste heat and eliminate the need for reactor coolers/condensers.

The reaction temperature of the tubular reactor of the invention is regulated by the boiling point of the heat transfer fluid. By varying the pressure of the heat transfer fluid, it is possible to vary the boiling point of the heat transfer fluid.

Despite the fact that the heat pipe equipped tubular reactor of the present invention adds intermediary steps to the overall heat transfer mechanism, the heat transfer flux of the heat pipe equipped reactor section can be enhanced by several fold from conventional immersed tube evaporative heat exchange. The fast rate of heat transfer with fluid evaporation on a porous surface and the rapid transport of the vapors away from the evaporator section to the condenser section of the heat pipe contribute to this superior performance.

In the reactor of the invention, the heat transfer fluid is chosen to assure trouble free heat pipe operation depending on the temperature of operation. It can be selected from liquids having the desired boiling point at a selected operating pressure. Common heat transfer fluids are water, acetone, alkanes, ammonia, fluorocarbons, aromatic solvents and even pure liquid metals.

The wick utilized in the invention can be comprised of fiber mats, sintered metal powders of spherical or non-spherical shape, of single size or multiple sizes, and metal screens in single or multiple layers, all with or without external surface enhancements, such as fins.

In most cases, the tube side of the reactor contains the solid pellets of catalyst through which gas reactants flow. The tube side of the reactor of the invention is unchanged from all conventional tubular reactors.

The heat pipe equipped tubular reactor of the invention can maintain isothermal conditions under appreciably large differences in heat flux. Such differences occur when a localized hot spot is started. Taking the partial oxidation reaction of ethylene to ethylene oxide as an example, a local hot spot will result in more complete oxidation of ethylene into carbon dioxide. This side reaction generates 12.6 times more heat than the desired reaction to ethylene oxide. The increased heat generated, if not removed, can lead to excessive reactor temperature which can cause a further deterioration of reactor selectively and even a deterioration of the heat transfer fluid on the shell side, which ultimately can ruin the entire reactor. A heat pipe equipped reactor of the invention responds to such high heat flux situation through increased evaporation rate at the same temperature. It therefore self regulates a runaway reaction.

The increased heat removal capability in the hot spot area of a tubular reactor is of great advantage. Localized hot spotting leading to runaway reaction is eliminated, despite intense heat generation. The conventional hump-shape temperature profile of an exothermic catalytic reaction is thus flattened and the reactor of the invention operates at an optimal selectivity.

The construction of the reactor of the invention is much simplified from that of the conventional tubular reactor. For example, in an ethylene oxide reactor using direct steam generation, the desired temperature may be 200° C. corresponding a steam pressure of 220 psia. However, due to hot spots commonly occurring in conventional ethylene oxide reactors, the reactor vessel must be designed for temperatures as high as 250° C., corresponding to a steam pressure that may be as high as 566 psia. High pressure design requirements greatly increase cost. For this reason, the use of water as a heat transfer fluid, which is inexpensive and beneficial from an operations perspective, must be sacrificed for a low boiling hydrocarbon based heat transfer fluid.

Another advantage of the present invention arises when by human error or instrument failure, the level of coolant is permitted to fall below its normal operating level in the reactor. In conventional reactors, hot spotting will quickly occur at the top of the reactor. If the reactor tubes of the reactor of the present invention are equipped with porous surface over their entire length or for at least a portion of their length beneath the reactor's normal coolant operating level, the reactor of the invention is more forgiving because the tube sections which are exposed by the falling coolant level switch from submerged operation to a heat pipe mode. The porous surface has a wicking action that can wet the tube surface.

The invention is not limited to the use of water as a heat transfer fluid. Any suitable liquid applicable to the reaction temperature can be used as a heat transfer fluid. With proper reactor design the temperature profile of the tubular reactor of the invention can be controlled to within 1 degree C. over the tube length.

The materials of construction in contact with the internal fluid can be copper and copper alloys, aluminum and alloys, various stainless steels or nickel alloys. Where the material in contact with the internal fluid is not compatible with the process liquid two different materials can be used in the form of plating, lining or coating. The internal liquids are chosen to assure trouble free heat pipe operation depending on the temperature range of operation. They can be selected from: water, acetone, alcanes, ammonia, fluorocarbons, aromatic solvents and pure liquid metals. The construction of the wick can be sintered metal powders of single size or multiple size, spherical or non-spherical shape, metal screens in single or multiple layers and with or without external surfaces.

A catalytic tubular reactor according to the invention, comprises tubes filled with porous pellets of catalyst. The catalyst containing tubes can be as long as approximately 35 feet to approximately 50 feet. Reactor tube length is governed by practical considerations such as assembly and service and is not critical to the invention. The bed temperature varies along the tube length and as a function of catalyst age. Generally, the reactor hot spot associated with the most active reactor section moves towards the reactor outlet as the catalyst in the reactor becomes less active over its operating life. To deal with reactor hot spots which move, the reactor of the invention is best equipped with heat pipe cooling systems over a tube length which corresponds to the reactor's expected hot spots when the catalyst in the reactor is new and also when it has aged.

BRIEF DESCRIPTION OF THE DRAWINGS

Specific embodiments of the present invention will now be described further, by way of example, with reference to the accompanying drawings, in which.

DETAIL DESCRIPTION OF THE INVENTION

Chemical reactors with heat pipe heat transfer devices and methods of using such devices to perform chemical reactions are disclosed. In the following detailed description of the invention, for purposes of explanation, specific features, materials, dimensions and the like may be set forth to provide a thorough understanding of the present invention. However, it will be apparent to those skilled in the art that the present invention may be practiced without these specific details. In some instances, well known devices are shown in simplified or block diagram form so as not to obscure the invention unnecessarily.

Figure 1:
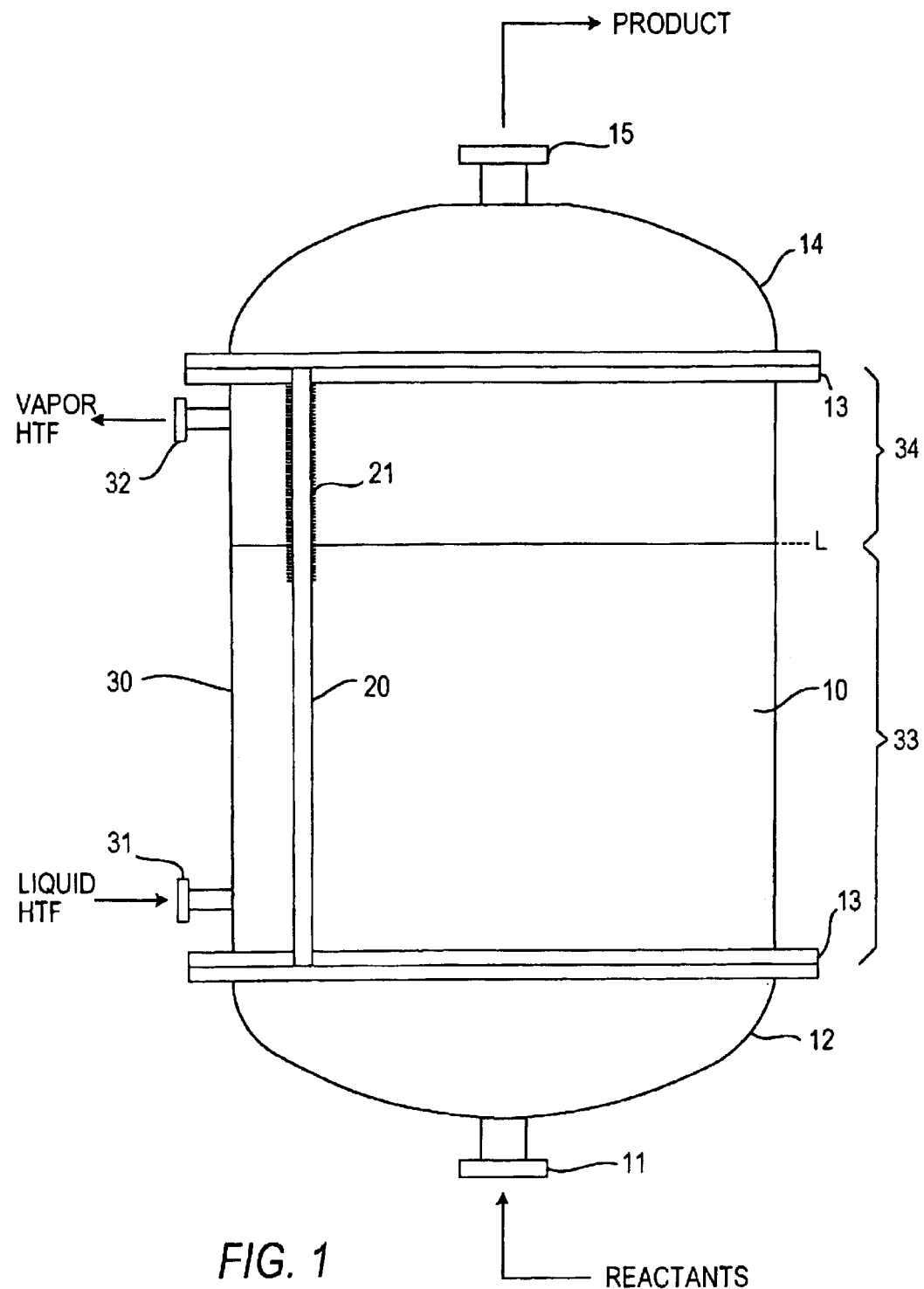
FIG. 1 illustrates a longitudinal cross section of a tubular reactor according to the invention having direct steam generation.

With reference to FIG. 1, a preferred embodiment of a tubular reactor 10 constructed according to the present invention is illustrated. For purposes of simplified illustration, reactor 10 is shown with a single reactor tube 20. A commercial reactor 10 could contain hundreds or thousands of tubes 20. Tube 20 is filed with porous catalyst pellets (not shown). Reactor 10 can be operated in an up- or downward flow pattern. For purpose of illustration, an upward flow is shown in FIG. 1. Reactants are fed into reactor 10 through input nozzle 11 which opens to reactor inlet head 12. Reactor inlet head 12 distributes the reactants to multiple tubes 20 mounted in tube sheets 13. Product from tubes 20 flows through reactor outlet head 14 to output nozzle 15.

Liquid heat transfer fluid ("HTF") is fed into shell 30 through HTF feed nozzle 31 and fills shell 30 to level L. Tube 20 is equipped with wick surface 21 at its outlet end. Liquid HTF level L divides reactor 10 into submerged tube zone 33 and heat pipe zone 34.

In zone 33, the HTF removes the heat of reaction by boiling. The heat flux capacity of tube 20 below liquid level L is significantly improved by the extension of wick surface 21 below liquid level L because the porous surface creates nucleating sites that promote boiling. However, a completely submerged reactor tube 20 will not act as a heat pipe even if it is equipped with wick surface 21 in the submerged section because heat pipe operation requires a vapor space in the area of wick surface 21 to enable the rapid transmission of vapor from the evaporator section of the heat pipe. For maximum heat transfer capacity and flexibility, the entire length of tube 20 may be covered with a porous surface, such as wick surface 21. Extension of wick surface 21 at least a small distance below liquid level L has the advantage of enabling heat pipe cooling of tube 20 in the event that the liquid level in shell 30 drops below L by reason of operator error or instrumentation failure. Wick surface 21 dips into the liquid HTF below level L and capillary action draws liquid HTF into wick surface 21. The heat of reaction causes the evaporation of the HTF on wick surface 21, which draws more wetting of wick surface 21 by capillary pumping. This auto cooling creates a uniform temperature even in the position of a hot spot. Evaporated HTF from submerged tube 20 in zone 33 and from wick surface 21 of tube 20 in zone 34 flows through vapor HTF outlet 32.

If the HTF is water, or another substance which finds application in the facility of reactor 10, the evaporated HTF can be conveyed to a steam or vapor header for a variety of uses. Alternatively, evaporated HTF can be condensed in a condenser (not shown) and the condensate returned by gravity or pumping to reactor 10 at HTF feed nozzle 31.

The length of heat pipe zone 34 is limited by the maximum capillary height. If necessary, several heat pipe zones may be present to cover a long section of tubular reactor. HTF reservoirs/distributors must be provided at the bottom of each heat pipe zone 34.

Figure 2:
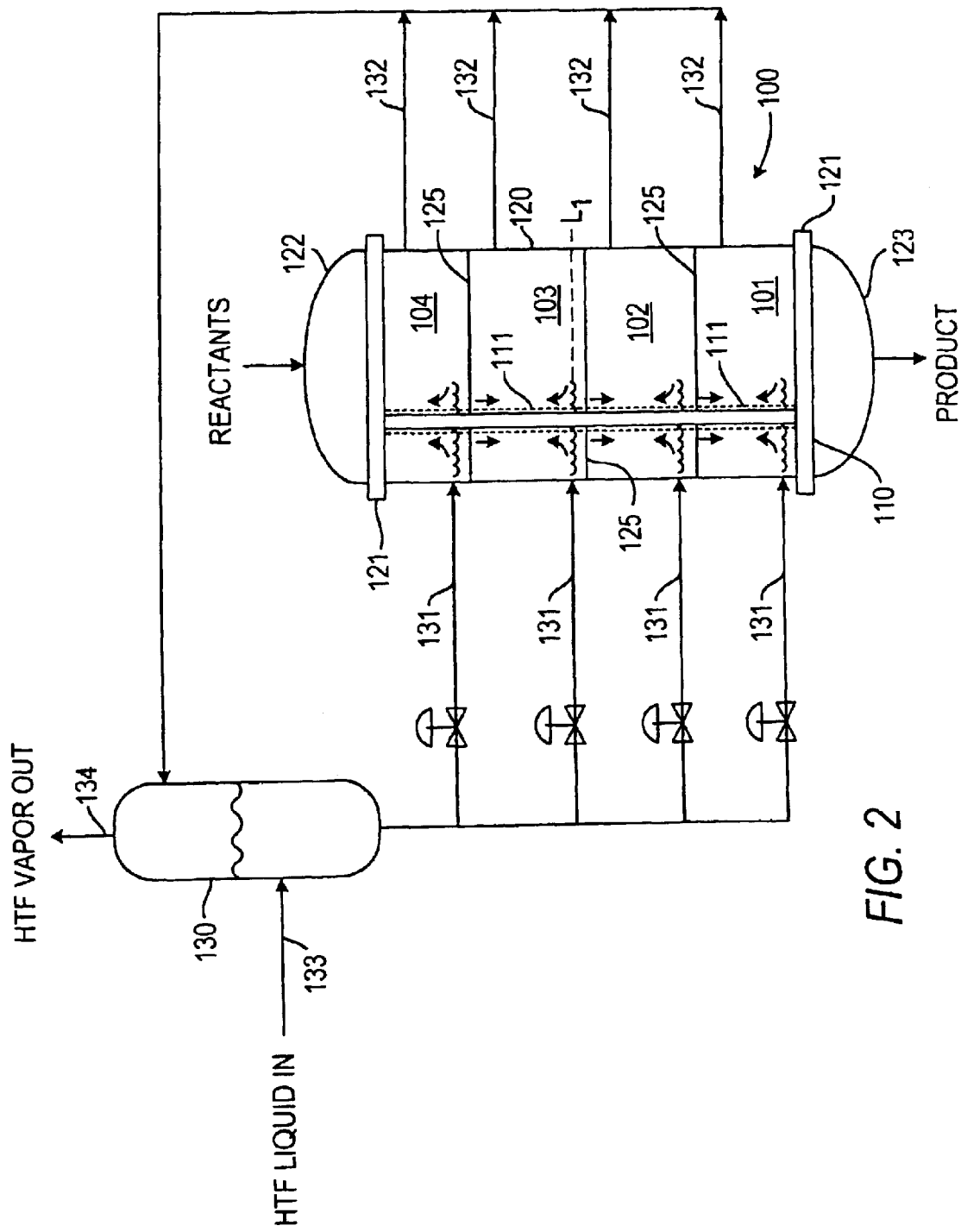
FIG. 2 illustrates a longitudinal cross section of a multizone tubular reactor according to the invention.
Figure 3:
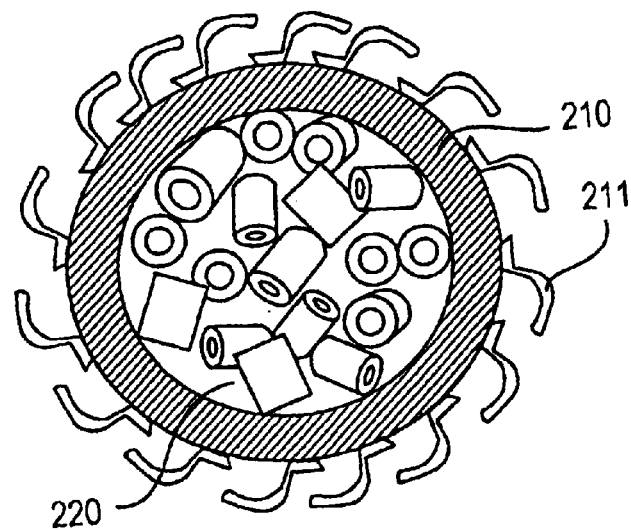
FIG. 3 illustrates a cross section of a finned reactor tube according to the invention.

Capillary action is commonly used in heat pipes. However for long vertical pipes exceeding a few feet, the surface tension on which capillary action relies is insufficient to overcome the hydrostatic pressure acting on a long vertical pipe. In such situations, an alternative embodiment of the invention shown in FIG. 2 is preferred. FIG. 2 shows a multizone tubular reactor 100 comprised of separate heat transfer fluid evaporating zones. For purposes of simplified illustration, reactor 100 is illustrated with one reactor tube 110 and four evaporation zones 101 to 104. A commercial reactor 100 could contain hundreds or thousands of tubes 110. Tubes 110 are filed with porous catalyst pellets 220, as shown in FIG. 3.

Tubes 110 are mounted in reactor shell 120 between tube sheets 121. Reactants are fed into the top of reactor 100 at reactor inlet head 122 and distributed among tubes 110. Reactants are shown to flow downwardly through porous catalyst pellets 220 in tubes 110 but can also flow in the reverse direction. Unconsumed reactants, product and any reaction by-products flow from the bottom of tubes 110 into reactor outlet head 123 and from there exit reactor 100.

Liquid HTF is introduced through conduit 133 to separator 130 and is distributed to heat pipe distributors 125 by HTF feed conduits 131. Distributors 125 are full baffle plates which are perforated to allow the passage of reactor tubes 110. The perforations in distributors 125 are not tightly fitted to tubes 110 so as to allow some liquid HTF to seep through wick surface 111 to the heat pipe zone below. Vapor HTF exits the top of evaporation zone 101 to 104 through conduits 132 and flows to entrainment separator 130 which acts also as a preheater for liquid heat transfer fluid feed 133. Porous wick surface 111 can be applied to tubes 110 in all of the evaporation zones 101 to 104, or alternatively in one or more of such zones.

Liquid HTF is maintained to level L1 on distributors 125 in zones 101 to 104 by controlling the flow of liquid HTF through control valves 135. Distributors 125 thereby serve as reservoirs of liquid HTF to wick surface 111 in each of evaporation zones 101 to 104 and to the wick surface below. Evaporated HTF exits separator 130 through vapor exit conduit 134.

In a tightly packed tube bundles it can be very difficult to distribute the liquid HTF evenly over the tubes. The use of one or several distributor 125 alleviates this problem.

Figure 4:
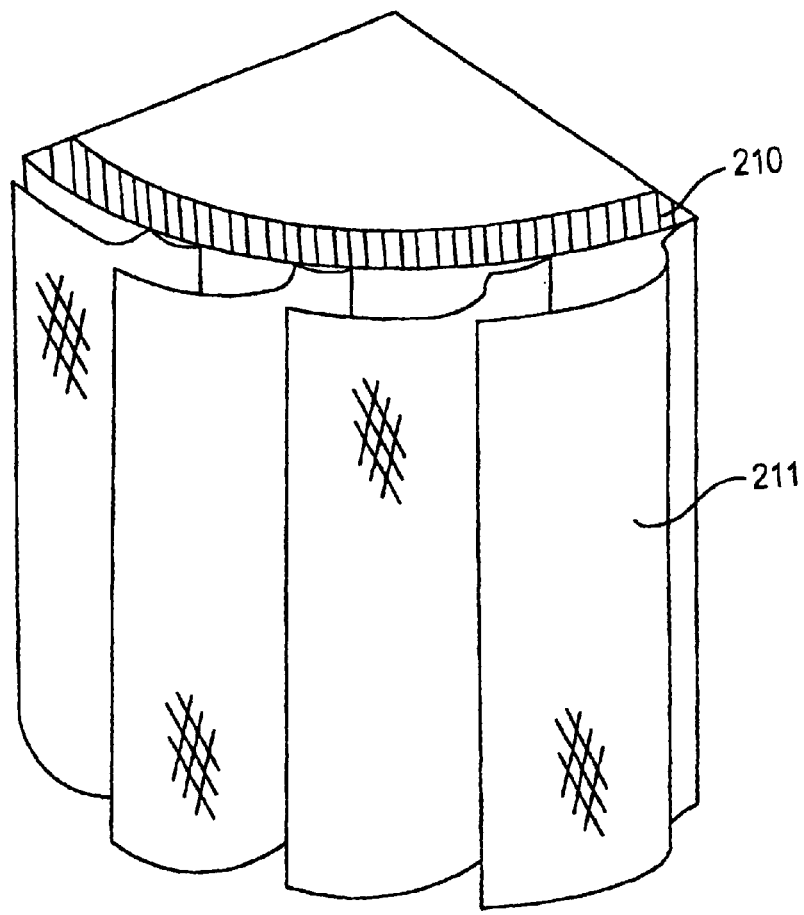
FIG. 4 illustrates a perspective view of a finned reactor tube according to the invention.

Wicked heat pipe surface 111 on the outside of reactor tubes 110 can consist of sintered metal powder of spherical or odd shape, sintered metal fibers, or metal mesh with or without fins. Mesh fins 211, as illustrated on tube 210 in FIGS. 3 and 4, can significantly increase the evaporation area and therefore reduce the heat flux in a particular zone of a reactor tube, such as a hot spot area where the heat flux might otherwise exceed the normal capacity provided by tubes 110.

The tubes of a reactor according to the invention can be of any size, but preferably are ¾ inch to 1.5 inch diameter seamless tubes. Although smaller diameter tubes increase the heat transfer area per unit of reaction volume, small tubes often provide low reactor volume usage due to poor catalyst packing and increase the probability for catalyst bridging. These problems can cause uneven flow distribution. Tube thickness is selected based on the process pressure. The tubes of a reactor according to the invention are made of metal compatible with the process chemicals. The thickness of wick surface 21 and wicked heat pipe surface 111 generally should not exceed 1 mm.

The above description of the invention is intended to be illustrative and not limiting. Various changes or modifications in the embodiments described may occur to those skilled in the art. These can be made without department from the spirit or scope of the invention.

I claim:

1. A tubular reactor for conducting chemical reactions having exothermic heat of reaction comprising:

at least one thermally conductive reactor tube extending between at least two tube plates in a heat exchanger shell;

said reactor tube having an open feed end for introducing reactants to a reaction zone in the interior of said reactor tube and an open exit end for conducting reaction products from said reactor tube;

said thermally conductive reactor tube having an exterior heat transfer tube surface between said tube plates and within said heat exchanger shell; and said exterior heat transfer tube surface having at least one heat pipe heat transfer device on it for conducting said exothermic heat of reaction from said thermally conductive reactor tube at essentially isothermal conditions.

2. The tubular reactor of claim 1, wherein said reactor tube has a length and a portion of said reactor tube length corresponds to a hot spot in said reaction zone characterized by heat generation which exceeds the average heat generation per unit of reactor tube length and wherein said heat pipe heat transfer device is positioned on said hot spot.

3. The tubular reactor of claim 1, wherein said reactor tube has a length and said heat pipe heat transfer device is on said reactor tube over substantially its entire length.

4. The tubular reactor of claim 1, wherein said reactor tube has a length, said heat exchanger shell contains a fluid reservoir for holding a liquid heat transfer fluid in a portion of said heat exchanger shell, said reactor tube extends through said fluid reservoir, and said heat pipe heat transfer device is on said reactor tube where it extends through said fluid reservoir and also extends along the length of said reactor tube beyond said fluid reservoir thereby enabling heat transfer fluid in said fluid reservoir to be wicked from said fluid reservoir by said heat pipe heat transfer device to an adjacent portion of said reactor tube.

5. The tubular reactor of claim 4, wherein said heat exchanger shell contains a plurality of spaced apart fluid reservoirs for holding liquid heat transfer fluid and said thermally conductive reactor tube extends through said plurality of fluid reservoirs, thereby defining a heat pipe heat transfer zones between said fluid reservoir.

6. The tubular reactor of claim 5, further comprising a means for conveying liquid heat transfer fluid to said fluid reservoirs.

7. The tubular reactor of claim 1, wherein said reactor tube is vertical in said heat exchanger shell.

8. The tubular reactor of claim 6, wherein said reactor tube is vertical in said heat exchanger shell.

9. The tubular reactor of claim 1, wherein said heat exchanger shell has a heat transfer fluid inlet for conveying liquid heat transfer fluid to said reactor tube and a heat transfer fluid outlet for conveying evaporated liquid transfer fluid from said heat exchanger shell.

10. The tubular reactor of claim 6, wherein said heat exchanger shell has a heat transfer fluid inlet for conveying liquid heat transfer fluid to said reactor tube and a heat transfer fluid outlet for conveying evaporated liquid transfer fluid from said heat exchanger shell.

11. The tubular reactor of claim 1, wherein said heat pipe heat transfer device comprises a porous heat transfer surface on said reactor tube.

12. The tubular reactor of claim 6, wherein said heat pipe heat transfer device comprises a porous heat transfer surface on said reactor tube.

13. The tubular reactor of claim 11, wherein said porous heat transfer surface is augmented by porous fins.

14. The tubular reactor of claim 12, wherein said porous heat transfer surface is augmented by porous fins.

* * * * *